United States Patent
Klingenbeck-Regn

(10) Patent No.: US 8,164,631 B2
(45) Date of Patent: Apr. 24, 2012

(54) METHOD FOR CONTROLLING THE MOVEMENT OF A MOBILE PART OF AN X-RAY RECORDING SYSTEM, AND AN X-RAY RECORDING SYSTEM COUPLED TO VIDEO CAMERAS

(75) Inventor: Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 956 days.

(21) Appl. No.: 12/171,637

(22) Filed: Jul. 11, 2008

(65) Prior Publication Data

US 2009/0015669 A1 Jan. 15, 2009

(30) Foreign Application Priority Data

Jul. 12, 2007 (DE) .......................... 10 2007 032 540

(51) Int. Cl.
*H04N 5/253* (2006.01)
*H04N 5/225* (2006.01)
(52) U.S. Cl. .......................................... 348/171; 348/77
(58) Field of Classification Search .................... 348/77, 348/171
See application file for complete search history.

(56) References Cited

U.S. PATENT DOCUMENTS

| | | | |
|---|---|---|---|
| 5,347,459 A | 9/1994 | Greenspan et al. | |
| 5,878,112 A * | 3/1999 | Koertge | 378/209 |
| 6,272,368 B1 * | 8/2001 | Alexandrescu | 600/407 |
| 6,927,395 B2 * | 8/2005 | Koops et al. | 250/363.08 |
| 7,428,296 B2 * | 9/2008 | Bernhardt et al. | 378/117 |
| 7,564,949 B2 * | 7/2009 | Sattler et al. | 378/117 |
| 7,720,198 B2 * | 5/2010 | Schliermann | 378/95 |
| 7,855,656 B2 * | 12/2010 | Maschke | 340/686.1 |
| 7,920,719 B2 * | 4/2011 | Hasegawa et al. | 382/103 |
| 7,949,096 B2 * | 5/2011 | Cheng et al. | 378/65 |
| 2006/0285644 A1 | 12/2006 | Camus | |

FOREIGN PATENT DOCUMENTS

DE 102005028215 A1 12/2006

OTHER PUBLICATIONS

Dirk Ebert, "Bildbasierte Erzeugung kollisionsfreier Transferbewegungen für Industrieroboter", Dissertation, Datum der Einreichung: Jun. 23, 2003, pp. I-VII, 1-131, Technische Universität Kaiserslautern, Fachbereich Informatik; Others.

* cited by examiner

*Primary Examiner* — Larry Donaghue

(57) ABSTRACT

With an x-ray imaging system with a moveable part, obstacles can stand in the way of the movement of the moveable part. In accordance with the invention, video cameras capture the occupation of the space by objects using volume elements. It is possible to determine at a target movement of the moveable part which volume elements are passed through during this. If one of these volume elements proves to be a volume element occupied by an object, the movement of the moveable part is prevented, otherwise it is enabled or actively implemented.

9 Claims, 1 Drawing Sheet

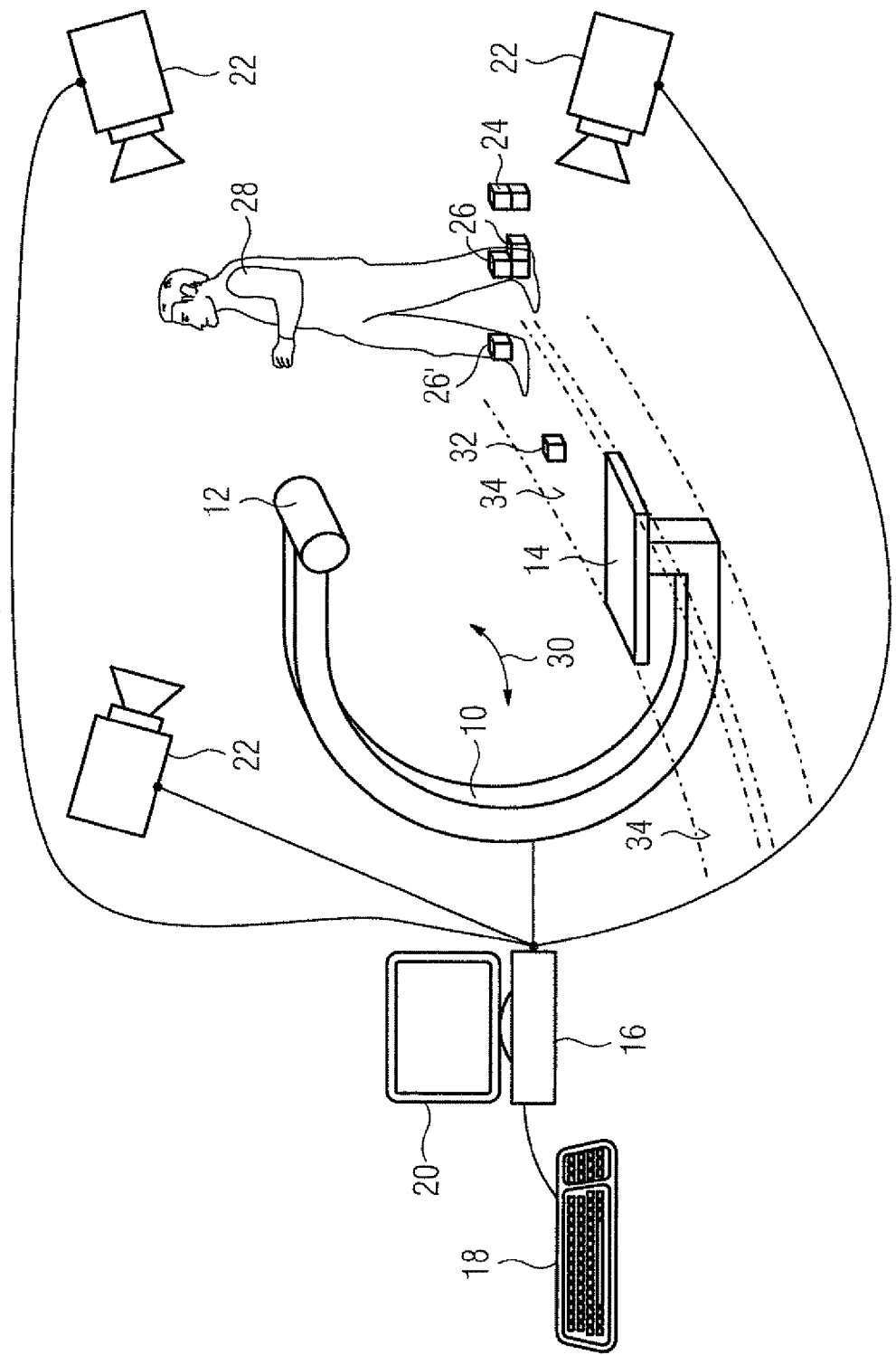

METHOD FOR CONTROLLING THE MOVEMENT OF A MOBILE PART OF AN X-RAY RECORDING SYSTEM, AND AN X-RAY RECORDING SYSTEM COUPLED TO VIDEO CAMERAS

CROSS REFERENCE TO RELATED APPLICATIONS

This application claims priority of German application No. 10 2007 032 540.3 filed Jul. 12, 2007, which is incorporated by reference herein in its entirety.

FIELD OF THE INVENTION

The invention relates to a method for controlling the movement of a moveable part of an x-ray imaging system as well as an x-ray imaging system.

The x-ray imaging system can be a conventional x-ray C-arm system and the moveable part is then the x-ray C-arm. The invention is also used in an x-ray imaging system, with which the x-ray tube and x-ray detector are moved by a robot.

BACKGROUND OF THE INVENTION

Modem x-ray imaging systems, in particular the x-ray C-arm systems, allow a plurality of movements of the respective moveable part. It is not easy for an operator to predict whether or not the moveable part meets with an obstacle during its movement. Such an obstacle can be the patient him/herself, an instrument table with instruments for performing interventions on the patient, a stand for a catheter system and many more.

To prevent the moveable part from causing an accident during its movement, a slow test run is regularly carried out, during which no imaging takes place and an imaging cycle is only implemented rapidly when the slow test run has been carried out smoothly.

The test run is time-consuming which is then particularly troublesome if the x-ray imaging system conducts an interventional operation on the patient, which is then namely delayed in its performance. In the event of a slow test run, this also does not guarantee that an accident of whatever nature does not take place despite the slow rate.

SUMMARY OF THE INVENTION

It is thus the object of the invention to provide a reliable method for controlling the movement of a moveable part of an x-ray imaging system which does not show the above-described disadvantages.

The object is achieved by a method and an x-ray imaging system with the features as claimed in the claims.

The method according to the invention thus includes the steps:
 providing a plurality of video cameras, which can capture at least one subarea of the space passed through by the moveable part during possible movements,
 dividing the space captured by the video cameras into a plurality of volume elements,
 capturing at each volume element whether it is occupied by an object or whether the volume element is object-free,
 defining a target movement of the moveable part (from a current position),
 determining which volume elements the moveable part would pass through during its target movement,
 checking whether at least one of the volume elements, which the moveable part would pass through during its target movement, belongs to the volume elements occupied by an object,
 and if yes: preventing the target movement,
 and if no: enabling the target movement.

A suitable number of video cameras (three to four units, preferably up to eight units) allows the space in which the x-ray imaging system is located to be more or less completely captured, at least the surroundings of the moveable part can be completely captured. It is as a result possible to make a prediction as to whether or not a collision of the moveable part with an obstacle would take place with the implementation of the target movement. This predictive function dispenses with the need for the slow test run. The cameras basically operate continuously. Provision can however be made for the cameras to be pivotable in order to capture certain regions in a targeted fashion, the cameras may however also be fixedly installed and hardly any time required for capturing the obstacles is lost particularly in the latter case. An operator can input a target movement of the moveable part, the system promptly checks whether an obstacle is present and in the absence of an obstacle, the target movement can be implemented immediately and/or promptly. Time is saved as a result, in comparison with the prior art, with which the slow test ran is implemented. In the event of the positive output of the examination such that at least one of the volume elements which the moveable part would pass through during its target movement belongs to the volume elements occupied by an object, the prevention of the target movement takes place by means of an optical, acoustic or haptic warning message to the operator, who then accordingly foregoes the target movement.

A typical type of target movement with an x-ray C-arm system is the circular arc movement for circular arc scanning. Here in particular, the slow test run takes place in the prior art and the invention is directly advantageous as a result of its above-cited time saving. The invention advantageously also allows predefined positions to be rapidly alternated. This is necessary with the so-called N level workflow: with a certain interventional operation on a patient, x-ray images are to be recorded from N different perspectives, namely alternately. The treating doctor determines certain working positions and then only needs to briefly operate the x-ray imaging system during the interventional operation so that the position is changed. When implementing the method according to the invention, the attending doctor is relieved of the task of examining whether the movement of the moveable part obstructs an obstacle in the interim. Instead, the examination is carried out more or less in real-time by means of the method according to the invention, depending on embodiments, thereby rendering it possible to alternate particularly quickly between the different predefined positions.

One development of the method according to the invention, which is likewise helpful and contributes to the time saving, includes detecting which object and/or which type of object would stand in the way during the implementation of the target movement on the basis of an image recognition method. The image recognition on one individual image of one of the video cameras is sufficient, however the information from all video cameras is preferably naturally evaluated. The result of the evaluation is communicated to the operator (on a monitor or acoustically). The operator quickly finds out which object (subject, person) obstructs the movement of the moveable part and can remove the object from the region in which the moveable object moves.

An image recording system also belongs to the invention, which is in particular embodied as an x-ray C-arm system and which includes a moveable part and is coupled at the same time to a plurality of video cameras. A control facility, which is used to actuate the moveable part, is designed in accordance with the invention to analyze the images of the video camera and on the basis of the analysis to enable or disable a target movement of the moveable part (i.e. either if necessary to release it and otherwise to keep it blocked or vice versa to terminate an existing release by means of blocking).

The analysis of the images of the video cameras is preferably carried out by means of the inventive method, i.e. an occupation of volume elements by objects is determined on the basis of images of the video cameras and is determined at a defined target movement of the moveable part (e.g. on the basis of a CAD model of the moveable part, which is stored in the control facility) it is determined which volume elements are passed through during the target movement and a check is then carried out to determine whether these volume elements were determined as occupied.

BRIEF DESCRIPTION OF THE DRAWINGS

A preferred embodiment of the invention is described below with reference to the drawing, with the FIGURE illustrating the arrangement to be provided in a treatment room in order to implement the method according to the invention and clarifying the functionality thereof.

DETAILED DESCRIPTION OF THE INVENTION

An x-ray C-arm system 10 is arranged in a treatment room, of which only the x-ray C-arm 10 with x-ray source 12 and x-ray flat panel detector 14 is shown by way of representation in the FIGURE. The movements of the x-ray C-arm are controlled by a control facility 16. The control facility 16 receives input signals by way of an input facility 18. By way of example, a joystick is shown for the input facility, the inputs can take place in a manner known also by way of pushbuttons, a computer mouse or a keyboard. Useful displays are shown on a monitor 20 for an operator.

A patient couch, upon which a patient rests during the operation, conventionally forms part of the x-ray C-arm. For reasons of clarity, the patient couch and patient are omitted in the FIGURE. A plurality of video cameras 22 is now arranged in the space in which the x-ray C-arm system is positioned. Three such video cameras 22 are shown in the FIGURE, the inventive system then operates particularly expediently if eight cameras are arranged in the space. The video cameras 22 are set up (or at least can be set up) such that they are able to capture surroundings of the x-ray C-arm 10 with the same. The images of the video cameras 22 are evaluated. The video cameras 22 are connected to the control facility 16 in the FIGURE, the image evaluation can however take place in a special facility. The result of the analysis must however in the latter case be made available to the control system actuating the x-ray C-arm, so that it is ultimately possible to recombine the systems to be evaluated to form a single control facility. The illustrated coupling of the video cameras 22 to the control facility 16 therefore represents the most natural instance.

The number of video cameras 22 and their alignment is now selected such that a three-dimensional item of information relating to the occupation of the space can be captured. A statement can be made on the basis of the images of several video cameras 22 at one volume element 22 as to whether this is occupied by an object or is completely object-free, i.e. is exclusively filled with air. In the FIGURE, the volume element 24 is free of objects. Other volume elements, namely volume elements 26, 26' are however occupied by a person 28.

The control facility 16 now detects on the basis of the images recorded by the video cameras 22 for all volume elements, for which this is possible, whether or not these are occupied by an object according to the type of person 28.

Within the scope of the treatment of the patient (not shown in the FIGURE), it now results that the x-ray C-arm 10 has to be moved, e.g. has to be pivoted in accordance with arrow 30. The x-ray C-arm 10 with the x-ray tube 12 and x-ray flat panel detector 14 naturally passes through volume elements 32 during its pivoting movement, which were previously not captured by the x-ray C-arm 10. The whole space 23 passed through by the flat panel detector 14 and the part of the x-ray C-arm 10 associated herewith during the movement according to arrow 30 is marked in the FIGURE with a dotted line. The control facility 16 has a CAD (Computer Aided Design) model of the x-ray C-arm, in particular also of the flat panel detector 14. A space model is used in the control facility 16. The control facility 16 now determines which volume elements 32, like for instance volume element 32, are passed through during the movement of the x-ray C-arm, which is desired (target movement). This quantity of volume elements is now subsequently examined so as to determine whether it belongs to volume elements 24, which are free of objects or whether it belongs to volume elements 26 and/or 26', which are occupied by an object. The FIGURE shows that the volume element 26' belongs to the intersection of the volume elements, which are at the same time occupied by an object 28, and were passed through during the target movement of the x-ray X-arm according to arrow 30. A single such volume element 26' is sufficient for the control facility 16 to identify that the movement of the x-ray C-arm had been obstructed. The control facility 16 thereupon emits a warning signal on the monitor 20 to the operator and can in particular also block the movement of the x-ray C-arm 10. If however there is no volume element according to the type of volume element 26', i.e. if the entire space passed through by the x-ray C-arm 10 during its target movement is free of obstacles, the movement of the x-ray C-arm is released. If necessary, provision can be made for the previously entered target movement to be immediately implemented after the release.

The control facility 16 can also implement a pattern recognition on the basis of the information relating to the volume element 26 and can thus recognize which type of object appears as an obstacle during the target movement of the x-ray X-arm 10. It is currently possible to detect for instance that the object 28 is a person and to output on the monitor 20 "Person blocking movement of the x-ray C-arm". The operator can then ask the person 28 to leave the swivel range of the x-ray C-arm 10. If the object 28 is a subject, this can be removed.

For representational reasons, only the swiveling motion backwards and forwards according to arrow 30 was mentioned as the movement possibility for the x-ray C-arm. The method according to the invention is also used in more complex target movements, in particular movement sequences. It is possible to work in the N-level mode with the aid of the one x-ray C-arm, with which the x-ray C-arm 10 captures certain working positions alternately. Prior to each change, the system checks whether an obstacle prevents the movement of the x-ray C-arm 10. As a rule that no obstacle is present, it is possible to rapidly move backwards and forwards between the individual operating positions.

The invention claimed is:

1. A method for controlling a movement of a moveable part of an x-ray imaging system, comprising:
    providing a video camera that records an image of a space passed through by the moveable part during the movement;
    dividing the space into a plurality of volume elements;
    detecting whether an object is occupied in the volume elements;
    defining a target movement of the moveable part;
    determining the volume elements that the moveable part pass through during the target movement;
    checking whether the volume elements that the moveable part pass through during the target movement are occupied by the object;
    preventing the target movement if the volume elements are occupied by the object; and
    enabling the target movement if the volume elements are not occupied by the object.

2. The method as claimed in claim 1, wherein an optical, acoustic or haptic warning message is sent to an operator for preventing the target movement.

3. The method as claimed in claim 1, wherein the target movement is implemented immediately if the volume elements are not occupied by the object.

4. The method as claimed in claim 1, wherein the x-ray imaging system is an x-ray system.

5. The method as claimed in claim 4, wherein the moveable part is an x-ray C-arm of the x-ray C-arm system.

6. The method as claimed in claim 1, wherein the target movement comprises a circular arc movement.

7. The method as claimed in claim 1, wherein the target movement comprises a movement from a predefined position to another predefined position.

8. The method as claimed in claim 1, wherein a type of the object occupied in the volume elements during the target movement is notified to an operator based on the image recorded by the video camera.

9. An x-ray imaging system, comprising:
    a moveable part;
    a video camera that records an image of a space passed through by the moveable part during a movement; and
    a control unit that:
        divides the space into a plurality of volume elements;
        detects whether an object is occupied in the volume elements;
        defines a target movement of the moveable part;
        determines the volume elements that the moveable part pass through during the target movement;
        checks whether the volume elements that the moveable part pass through during the target movement are occupied by the object;
        prevents the target movement if the volume elements are occupied by the object; and
        enables the target movement if the volume elements are not occupied by the object.

* * * * *